United States Patent
Yang et al.

(10) Patent No.: US 10,500,314 B2
(45) Date of Patent: Dec. 10, 2019

(54) FLEXIBLE SUBSTRATE/LIQUID ELECTROLYTE VISCOUS COMPOSITE MATERIAL AND PREPARATION METHOD THEREFOR

(71) Applicant: SOOCHOW UNIVERSITY, Suzhou (CN)

(72) Inventors: Lei Yang, Suzhou (CN); Ning Sun, Suzhou (CN); Xiao Lin, Suzhou (CN); Wei Jiang, Suzhou (CN); Xinhong Wang, Suzhou (CN); Yanjie Bai, Suzhou (CN); Huilin Yang, Suzhou (CN); Aobing Bai, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 15/777,203

(22) PCT Filed: Apr. 26, 2016

(86) PCT No.: PCT/CN2016/080288
§ 371 (c)(1),
(2) Date: May 17, 2018

(87) PCT Pub. No.: WO2017/177480
PCT Pub. Date: Oct. 19, 2017

(65) Prior Publication Data
US 2018/0333517 A1     Nov. 22, 2018

(30) Foreign Application Priority Data
Apr. 15, 2016 (CN) .......................... 2016 1 0234727

(51) Int. Cl.
| | | |
|---|---|---|
| *A61L 27/58* | (2006.01) | |
| *A61L 27/44* | (2006.01) | |
| *A61L 27/50* | (2006.01) | |
| *A61L 27/04* | (2006.01) | |
| *A61L 27/20* | (2006.01) | |
| *A61L 27/22* | (2006.01) | |
| *A61L 27/54* | (2006.01) | |

(52) U.S. Cl.
CPC ............. *A61L 27/58* (2013.01); *A61L 27/047* (2013.01); *A61L 27/20* (2013.01); *A61L 27/222* (2013.01); *A61L 27/446* (2013.01); *A61L 27/50* (2013.01); *A61L 27/54* (2013.01); *A61L 2430/20* (2013.01)

(58) Field of Classification Search
CPC ........ A61L 27/58; A61L 27/446; A61L 28/50; A61L 27/047; A61L 27/20; A61L 27/222; A61L 27/54; A61L 2430/20
See application file for complete search history.

(56) References Cited

U.S. PATENT DOCUMENTS

2014/0353248 A1* 12/2014 Oka ........................... C08J 9/28
210/616

FOREIGN PATENT DOCUMENTS

| CN | 101618236 A | | 1/2010 | |
|---|---|---|---|---|
| CN | 102178984 | * | 9/2011 | ............. A61L 27/20 |
| CN | 102178984 A | | 9/2011 | |
| CN | 103480037 A | | 1/2014 | |
| CN | 104189958 A | | 12/2014 | |
| CN | 104436305 A | | 3/2015 | |
| WO | WO-2007066837 A1 | * | 6/2007 | ............. A61K 8/733 |
| WO | 2015019109 A1 | | 2/2015 | |

* cited by examiner

Primary Examiner — Sean M Basquill
(74) Attorney, Agent, or Firm — SZDC Law P.C.

(57) ABSTRACT

Disclosed is a flexible substrate/liquid electrolyte viscous composite material and preparation method therefor. The preparation method includes: adding a particular percentage by weight of a flexible substrate to a liquid electrolyte solution having a particular concentrate; fully stirring the solution at a particular temperature to dissolve and evenly disperse the substrate, so as to obtain a viscous liquid; and then standing the viscous liquid at a particular temperature for a particular period of time to obtain the material. The material has viscosity due to which the material can actively adhere to the surface of tissue of an organ, the mechanical property matching cardiac muscle, biocompatibility and security, and is used for treating acute and chronic myocardial infarction and heart failures, inhibiting the reconstruction, thinning, and fiberization of a ventricular wall, and improving the myocardial function. In addition, the material also features conductivity, in vivo degradability, and the like.

3 Claims, 1 Drawing Sheet

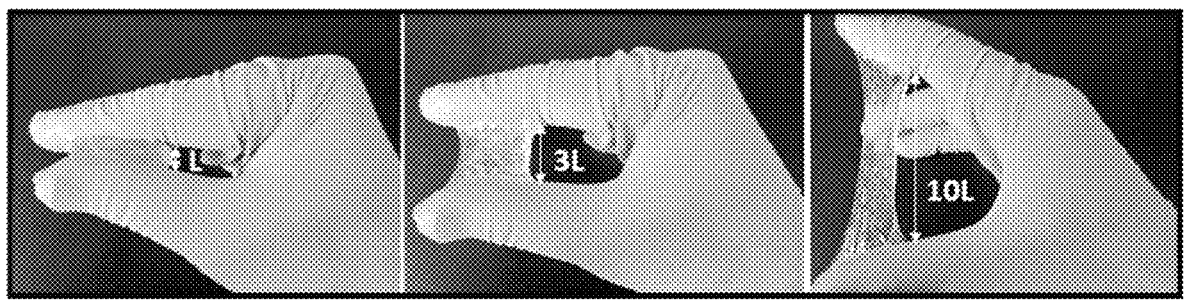

FLEXIBLE SUBSTRATE/LIQUID ELECTROLYTE VISCOUS COMPOSITE MATERIAL AND PREPARATION METHOD THEREFOR

This application is the National Stage Application of PCT/CN2016/080288, filed on Apr. 26, 2016, which claims priority to Chinese Patent Application No. 201610234727.5, filed on Apr. 15, 2016, which is incorporated by reference for all purposes as if fully set forth herein.

FIELD OF THE INVENTION

The present invention relates to a kind of biomedical material and the preparation method thereof. Particularly, the present invention relates to a material (and its preparation method) that could be stuck on the outer surface of epicardium for the treatment of myocardium infarction and heart failure caused by different factors. The present invention relates to the field of biomedical materials and its application.

TECHNICAL BACKGROUND

The heart failure caused by myocardium infarction and other factors (toxic substance, drugs, alcohol, genetic variation, gene mutation, virus or bacterial infection) is a major reason for death. According to statistics, the deaths caused by chronic heart failure and myocardium infarction account for more than 50% of total deaths caused by cardiovascular diseases. Additionally, the population suffered from the heart failure and myocardium infarction become younger, which has attracted a lot of attention from medical field.

The thrombosis of coronary artery, or genetic variations or mutation of pertinent genes, or the effect of toxic substance, drugs, alcohol, virus or bacterial infection can cause the death of some of the cardiomyocytes, which cannot regenerate, causing the irreversible injury of myocardium. Then the ventricle gets remodeled, leading to the thinning of ventricular wall, accompanied by the proliferation of fibroblasts and formation of scar tissue. Consequently, the functionality of myocardium decreased gradually, leading to the heart failure eventually. Recent studies showed that the remodeling of the ventricle could be inhibited by patching a soft material to strengthen the ventricular wall and prevent the proliferation of fibroblasts and formation of fibrosis tissue, improving the functionality of myocardium. Possible mechanisms include, (1) improving local mechanical microenvironment of myocardium, inhibiting fibroblast proliferation, promoting myocardial regeneration and angiogenesis; (2) increasing wall thickness, reducing ventricular wall pressure, stabilizing ventricular size, remodeling ventricular geometry, and preventing ventricular aneurysm formation.

The early studies used devices to wrap both of the ventricles, such as the Acorn CorCap and Paracor HeartNet ventricle support device. Then the left ventricle support devices, such as Myocor Coapsys and CardioClasp, were developed. The implantation procedures of the above devices are very complicated. Additionally, the size of these devices is too large that will cause harmful influence on the normal myocardium through contacting effect. In the recent years, researchers developed strengthening materials which was locally implanted to the myocardium that suffered from myocardial infarction. For example, Fujimoto et al sutured a PEUU film on the myocardium of rat heart with acute infarction (Ref. An Elastic, Biodegradable Cardiac Patch Induces Contractile Smooth Muscle and Improves Cardiac Remodeling and Function in Subacute Myocardial Infarction, 2007). Liao et al sutured a commercial double-layered film on the surface of ventricle with chronic infarction (Ref. Attenuation of Left Ventricular Adverse Remodeling with Epicardial Patching after Myocardial Infarction, 2010). Chi et al glued chitosan-hyaluronan/silk fibroin patches on the surface of ventricle of rat with chronic myocardial infarction (Ref. Cardiac Repair Using Chitosan-hyaluronan/silk Fibroin Patches in A Rat Heart Model with Myocardial Infarction, 2013).

The studies all reported positive results, proving the evidence of treating myocardial infarction by strengthening the myocardium with biomaterials. However, some limitations exist for the present materials. Firstly, the biomaterials used so far are not sticky and must be sutured on the surface of ventricle, which on one hand leads to the complexity of surgery, increasing the risk and causing injuries to the myocardium and on the other hand causes the local stress concentration on the myocardium. Secondly, the myocardium is characterized by fast relaxation and relatively slow creep. While different from myocardium, the present biomaterials are mostly elastic and this mismatch in mechanical property will induce the disorder of heartbeat. Thirdly, most of the present materials are not degradable in vivo nor degrade fast enough, which leads to the foreign body reaction from the host tissue. Lastly, the present patching materials are not injectable and need to be implanted though open-chest surgery, which is a complicated surgery with high risk.

SUMMARY OF THE INVENTION

The objective of this invention is to supply a kind of biodegradable, bio-safe, conductive and highly sticky and flexible substrate/liquid electrolyte composite, which owns mechanical properties matching well with myocardium, and preparation method thereof in order to overcome the disadvantages of current biomaterials for treating heart failure (caused by myocardium infarction and other factors), including mismatched mechanical properties with myocardium, lack of stickiness to the epicardium.

The technical solution to realize the objective is as follows.

A flexible substrate/liquid electrolyte viscous composite material, whose bonding strength with the surface of organ tissue is higher than 0.1 kPa, and the ratio of loss modulus to storage modulus of said material is 0.2 to 5 when tested at 37° C., oscillation frequency at 0.01 to 100 Hz, strain at 0.01 to 10; at 37° C., the elastic tensile strength of said material is 3 to 100 kPa, and the elongation to fracture is more than 50%, the time for reaching the 10% stress relaxation rate is less than 10 min; at 37° C., the electric conductivity is between 0.01 and 10 S/m, the cytotoxicity level of material extract is 0 to 1.

In the present invention, said flexible substrate is one of fibril gel, dopamine, gelatin, hyaluronic acid, starch, alginate or any combination thereof.

In the present invention, said liquid electrolyte is solution of either of zinc nitrate, lithium nitrate, calcium nitrate, magnesium nitrate, potassium nitrate, lithium chloride, calcium chloride, zinc chloride, magnesium chloride, calcium iodine or any combination thereof. When patching at the surface of epicardium in vivo, said composite material degrades within 6 to 24 months.

The present invention also includes a preparation method of said flexible substrate/liquid electrolyte viscous composite material, comprising the following steps:

(1) according to the mass percent of 10% to 20%, dissolving the metallic salt into deionized water to form an electrolyte solution;

(2) according to the mass percent of 3% to 10%, mixing flexible substrate into the electrolyte solution prepared in step (1), then stirring at the temperature between 25 and 80° C. to form a viscous liquid;

(3) aging the viscous liquid obtained in step (2) between 25 and 45° C. until the material achieving a stable state, to obtain the flexible substrate/liquid electrolyte viscous composite material.

In the present invention, said metallic salt is either of zinc nitrate, lithium nitrate, calcium nitrate, magnesium nitrate, potassium nitrate, lithium chloride, calcium chloride, zinc chloride, magnesium chloride, calcium iodine or any combination thereof. Said flexible substrate is either of fibril gel, dopamine, gelatin, hyaluronic acid, starch, alginate or any combination thereof.

The present invention supplies an application of said flexible substrate/liquid electrolyte viscous composite material in the treatment of heart failure caused by myocardium infarction and other factors, comprising the following steps:

1. Accessing to ventilator after anaesthesia.

2. Opening the chest to expose heart under the sterile condition after breathing steadily; making sure the required amount of sticky composite according to the size of myocardium infarction and the degree of cardiac insufficiency.

3. Patching proper amount of sticky composite on the surface of epicardium of heart infarction zone or ventricle with heart failure, without additional fixation.

4. Closing the chest, removing the ventilator after regaining autonomous respiration.

5. The sticky composite degrades after the treatment cycle, without need to remove though operation.

The present invention supplies another application of flexible substrate/liquid electrolyte viscous composite material for the treatment of heart failure caused by myocardium infarction and other factors, comprising the following steps:

1. Identifying the location and area of infarction zone though coronary angiography, thoracoscopic observation or echocardiogram, making sure the required amount of sticky composite according to the size of myocardium infarction and the degree of cardiac insufficiency.

2. Guided by the thoracoscope or X-ray machine, using injection devices or minimally invasive surgical forceps to deliver certain amount of sticky composite though working channel of minimally invasive surgery on the surface of epicardium of heart infarction zone or ventricle with heart failure, without additional fixation.

3. Withdrawing the delivery devices, closing the wound after the sticky composite forming an intact piece of film on the surface of epicardium of heart infarction zone or ventricle with heart failure, and finishing the operation.

4. The sticky composite degrades after the treatment cycle, without need to remove though operation.

Compared with prior arts, this invention has following advantages:

1. The raw materials for preparing said composite are low cost. The composite is simple to prepare and the preparation method is environmentally friendly.

2. The composite owns mechanical properties matching well with myocardium, and is highly conductive, bio-safe, bio-degradable, thus is suitable for myocardial infarction treatment and matching well with the myocardium morphologically, mechanically and electrophysiologically.

3. The composite is convenient to use due to its stickiness to tissue, avoiding the additional fixing procedure like suturing. This is beneficial for the clinical operation and also causes little additional damage to the normal myocardium. In addition, the said composite can be used in minimally invasive surgery.

BRIEF DESCRIPTION OF THE DRAWINGS

FIG. 1 is a photo showing the stickiness and stretchability of the sticky and flexible substrate/liquid electrolyte composite prepared in Embodiment 1.

DETAILED DESCRIPTION OF THE INVENTION

Embodiment 1

An electrolyte solution was prepared by dissolving calcium chloride in deionized water with mass percent of 18%. Then corn starch was added in the electrolyte with mass percent of 6% and was continuously stirred at 50° C., to obtain a viscous liquid. Then let the viscous liquid standing at 40° C. for 48 h, forming a high sticky and flexible conductive composite.

FIG. 1 is a photo showing the stickiness and stretchability of the sticky and flexible substrate/liquid electrolyte composite prepared above (L=1.2 mm). The photo shows that the composite stuck firmly on the surface of surgical latex glove, and could be stretched 10 times of original length, indicating the good stickiness and stretchability (more than 1000%). As measured at 37° C., the bonding strength between material and epicardium is 0.5~1 kPa, the tensile strength is 3~10 kPa, stretch ratios at fracture is 100%~1500%. The time for achieving 10% stress relaxation is 30~100 s. When test at oscillation frequency of 1~100 Hz and strain of 1%, the ratio of loss modulus to storage modulus of sticky composite is 0.8~1.5. At 37° C., the electric conductivity is 0.2~1.8 S/m. The cytotoxicity level of material extracts to NIH3T3 fibroblast is within 0~1 grade. After patching the material on the surface of heart of Sprague Dawley (SD) rats for 6 months, the histology analysis shows no obvious toxicity, inflammation reaction and severe immunological rejection.

The myocardial ischemia induced acute infarction model in SD rats was used. The SD rats were divided into two groups: experiment group and control group. No treatment was done for the control group. For the experiment group, the sticky composite was implanted following the procedures: opening the chest to expose the myocardium infarction or the cardiac insufficiency site and making sure the required amount of sticky composite based on the size of myocardium infarction and the degree of cardiac insufficiency; taking certain amount of sticky composite with surgical forceps and patching the sticky composite on the surface of epicardium of heart infarction zone or ventricle with heart failure into a required shape, size and thickness with surgical forceps; pressing the material slightly to make it sticking firmly on the heart surface without additional fixation; closing the chest, leaving the material in vivo to play the therapeutic effect.

The details of operation are as follows:

(1) Male SD rats weighing about 250 g are placed in a gas anesthetized chamber and anesthetized with 5% isoflurane;

(2) The rats access to ventilator, respiratory rate is 75 beats/min, respiratory ratio is 1:1 and isoflurane concentration is maintained at 2%;

(3) Open the chest after the rats breathe smoothly, expose the heart and open the pericardium, ligate the left anterior descending artery with 7-0 silk suture and determine the success of myocardial ischemia after observing the apex becomes white;

(4) About 0.1 g of the material provided in this example was gripped with tweezers and stretched to a thickness of about 0.5 mm and applied to the surface of the left ventricular ischemic site;

(5) Exclude the gas inside the chest, suture to close the chest;

(6) Turn off the gas anesthesia until the rats have autonomous respiration, then closed ventilator and intraperitoneal injection of 200 thousand units of penicillin.

The left ventricular diameter at the end of diastole (LVIDd) and left ventricular diameter at the end of systole (LVIDs) were measured using echocardiography every other week. The left ventricular ejection fraction (LVEF) and the left ventricular fractional shortening (LVFS) were calculated to evaluate the cardiac function in rats. Four weeks later, the rat heart was obtained, and the treatment group showed that the material still stuck on the left ventricular surface of the rat. Rat myocardial infarct size and degree of fibrosis were analyzed by hematoxylin and eosin (HE) staining and Masson trichrome staining.

Results:

(1) The fourth week of echocardiography shows that the LVIDd and LVIDs of the treatment group affixed with the material of this material were 6.2-6.5 mm and 3.6-4.3 mm respectively, while the two values of the control group were 8.5-9 mm and 8-8.6 mm respectively. The LVEF of the treatment group and the control group were 60-65% and 45-50% respectively, and the LVFS were 32-36% and 21-26% respectively, indicating that the heart function of the rats in the treatment group was restored to some extent.

(2) By HE and Masson staining we can see the material treatment group left ventricular wall thickness was 3.5~3.8 mm, while the control group was 2.4~2.6 mm, and the treatment group myocardial infarction area decreased by 70% to 76%, while the control group was 40% to 45%. It can be seen that the treatment group well inhibits the process of myocardial remodeling after myocardial ischemia and has a good therapeutic effect on myocardial infarction. Eight months after the operation, the material still adhered to the epicardium and degraded about 60-65%.

Embodiment 2

An electrolyte solution was prepared by dissolving calcium chloride, magnesium nitride and calcium nitride in deionized water with total mass percent of 15%. Then hyaluronic acid was added in the electrolyte with mass percent of 8% and was continuously stirred at 25° C., to obtain a viscous liquid. Then let the viscous liquid standing at 35° C. for 36 h, forming a sticky and flexible conductive composite.

The bonding strength between composite and epicardium is 0.1~0.5 kPa. When test at oscillation frequency of 0.1~100 Hz, strain at 2%, the ratio of loss modulus to storage modulus of the composite is 0.4~0.8. The tensile strength and stretch ratio at fracture are 10~15 kPa and 50%~150%. The time for achieving 10% stress relaxation is 100~300 s. The electric conductivity is 0.01~0.12 S/m. The cytotoxicity level of material extracts to NIH3T3 fibroblast is within 0~1 grade. After patching the material on the surface of heart of SD rats for 6 months, the histological analysis shows no obvious toxicity, inflammation reaction and severe immunological rejection.

The myocardial ischemia induced chronic infarction model in SD rats was used. The SD rats were divided into two groups: experiment group and control group. No treatment was done for the control group. For the experiment group, the material was implanted following the procedures: identifying the location and area of infarction zone though coronary angiography, thoracoscopic observation or echocardiogram and making sure the required amount of sticky composite based on the size of myocardium infarction and the degree of cardiac insufficiency; guided by the thoracoscope or X-ray machine, using injection devices or minimally invasive surgical forceps to deliver certain amount of sticky composite though working channel of minimally invasive surgery on the surface of epicardium of heart infarction zone or ventricle with heart failure, without additional fixation; withdrawing the delivery devices and closing the wound after the sticky composite forming an intact piece of film on the surface of epicardium of heart infarction zone or ventricle with heart failure, and finishing the operation. The sticky composite degrades after the treatment cycle, without need to remove though operation.

The details of operation are as follows:

(1) Chronic myocardial infarction rats were placed in a gas anesthetized chamber and rats were anesthetized with 5% isoflurane;

(2) Coronary angiography and echocardiography were performed in rats to determine the location and extent of myocardial infarction and the amount of material used;

(3) The rats were accessed to ventilator, with respiratory rate being 75 beats/min and respiratory ratio being 1:1. And isoflurane concentration was maintained at 2%;

(4) Implant material to the epicardium to be treated, exit the delivery system and close the wound;

(5) Turn off the gas anesthesia until the rats have autonomous respiration, then closed ventilator and intraperitoneal injection of 200 thousand units of penicillin.

The LVIDd and LVIDs was measured using echocardiography every other week. The LVEF and LVFS were calculated to evaluate the cardiac function in rats. Four weeks later, the rat heart was obtained, and the treatment group showed that the material still sticky to the left ventricular surface of the rat. Rat myocardial infarct size and degree of fibrosis were analyzed by HE and Masson trichrome staining.

Results:

(1) LVIDd and LVIDs of the treated group were lower than those of the control group in the fourth week while LVFS of the LVEF in the treated group were higher than that of the control group, indicating that the cardiac function of the rats in the treated group was recovered to some extent. (2) The left ventricular wall thickness of the treated group was significantly higher than that of the control group by staining, and the reduction of myocardial infarction area in the treatment group was also significantly higher than that of the control group, indicating that the material represses the ventricular remodeling process better. Four weeks after the operation, it was found that the material still adhered to the epicardial tissue and showed a complete laminar appearance. Eight months after the operation, the material still adhered to the epicardium and degraded about 40~50%.

What we claim is:

1. A flexible substrate/liquid electrolyte viscous composite biomedical material for the treatment of myocardium infarction and heart failure, consisting of:
   a flexible substrate selected from the group consisting of and corn starch; and
   a liquid electrolyte is a solution containing one selected from the group consisting of zinc nitrate, lithium nitrate, calcium nitrate, magnesium nitrate, potassium nitrate, lithium chloride, calcium chloride, zinc chloride, magnesium chloride, calcium iodine, and a combination thereof,
   wherein the material's bonding strength with the surface of organ tissue is higher than 0.1 Kpa, and the ratio of loss modulus to storage modulus of said material is 0.2 to 5 when tested at 37° C., oscillation frequency at 0.01 to 100 Hz, strain at 0.01 to 10; at 37° C., the elastic tensile strength of said material is 3 to 100 kPa, and the elongation to fracture is more than 50%, the time for reaching the 10% stress relaxation rate is less than 10 min; at 37° C., the electric conductivity is between 0.01 and 10 S/m, the cytotoxicity level of material extract is 0 to 1; and
   wherein the flexible substrate/liquid electrolyte viscous composite biomedical material is adapted for the treatment of myocardium infarction and heart failure.

2. A preparation method of the flexible substrate/liquid electrolyte viscous composite material according to claim 1, comprising the following steps:
   (1) according to the mass percent of 10% to 20%, dissolving the metallic salt into deionized water to form an electrolyte solution;
   (2) according to the mass percent of 3% to 10%, mixing flexible substrate into the electrolyte solution prepared in step (1), then stirring at the temperature between 25 and 80° C. to form a viscous liquid;
   (3) aging the viscous liquid obtained in step (2) between 25 and 45° C. until the material achieving a stable state, to obtain the flexible substrate/liquid electrolyte viscous composite material.

3. The preparation method of the flexible substrate/liquid electrolyte viscous composite material according to claim 2, wherein said metallic salt is either of zinc nitrate, lithium nitrate, calcium nitrate, magnesium nitrate, potassium nitrate, lithium chloride, calcium chloride, zinc chloride, magnesium chloride, calcium iodine or any combination thereof.

* * * * *